United States Patent [19]
Wilhelm et al.

[11] Patent Number: 5,715,327
[45] Date of Patent: Feb. 3, 1998

[54] METHOD AND APPARATUS FOR DETECTION OF UNSUITABLE CONDITIONS FOR AUTOMATED CYTOLOGY SCORING

[75] Inventors: Paul S. Wilhelm, Kirkland; Shih-Jong J. Lee, Bellevue, both of Wash.

[73] Assignee: NeoPath, Inc., Redmond, Wash.

[21] Appl. No.: 309,117

[22] Filed: Sep. 20, 1994

[51] Int. Cl.⁶ .................................................. G06K 9/00
[52] U.S. Cl. ..................... 382/128; 382/133; 364/413.1; 364/555; 435/7.2; 359/397
[58] Field of Search .................................. 382/128, 133; 364/413.1, 555; 435/7.2; 424/3; 359/397; 356/372

[56] References Cited

U.S. PATENT DOCUMENTS

| | | | |
|---|---|---|---|
| 3,824,393 | 7/1974 | Brain | 250/339 |
| 3,922,532 | 11/1975 | Kitchener et al. | 364/555 |
| 4,175,860 | 11/1979 | Bacus | 356/39 |
| 4,182,046 | 1/1980 | Ludlow et al. | 33/366 |
| 4,190,314 | 2/1980 | Goldsmith | 359/397 |
| 4,354,501 | 10/1982 | Colley et al. | 128/663 |
| 4,354,502 | 10/1982 | Colley et al. | 128/663 |
| 4,523,278 | 6/1985 | Reinhardt et al. | 382/133 |
| 4,538,299 | 8/1985 | DeForest | 382/21 |
| 4,741,043 | 4/1988 | Bacus | 382/133 |
| 4,842,900 | 6/1989 | Miyamoto | 427/328 |
| 4,965,725 | 10/1990 | Rutenberg | 364/413.1 |
| 5,058,181 | 10/1991 | Ishihara et al. | 382/22 |
| 5,173,946 | 12/1992 | Rao | 382/22 |
| 5,182,938 | 2/1993 | Merkel | 73/19.05 |
| 5,196,350 | 3/1993 | Backman et al. | 436/501 |
| 5,235,522 | 8/1993 | Bacus | 382/133 |
| 5,257,182 | 10/1993 | Luck et al. | 364/413.1 |
| 5,287,272 | 2/1994 | Rutenberg et al. | 364/413.1 |
| 5,315,700 | 5/1994 | Johnston et al. | 395/163 |
| 5,361,140 | 11/1994 | Hayenga et al. | 358/446 |
| 5,428,690 | 6/1995 | Bacus et al. | 382/128 |
| 5,499,097 | 3/1996 | Ortyn et al. | 356/372 |

OTHER PUBLICATIONS

Bacus, James W. and Les J. Grace, "Optical Microscope System For Standardized Cell Measurements and Analyses", *Applied Optics*, 26:16, pp. 3280–3293, 15 Aug. 1987.

Bartels, Peter H. et al., "A Self-Learning Computer Program for Cell Recognition", *ACTA Cytologica: The Journal of Clinical Cytology*, 14:8, pp. 486–494, Oct. 1970.

Duda, Richard O. and Peter E. Hart, "Fisher's Linear Discriminant", *Patent Classification and Scene Analysis*, Copyright ©1973, pp. 114–119.

Tanaka, Noboru et al., "Automated Cytologic Screening System (CYBEST Model 4): an Integrated Image Cytometry System", Reprinted from *Applied Optics*, vol. 26, p. 3301, Aug. 15, 1987. Copyright © 1987 by the Optical Society of America and reprinted by permission of the copyright owner.

(List continued on next page.)

*Primary Examiner*—Jose L. Couso
*Assistant Examiner*—Anh Hong Do
*Attorney, Agent, or Firm*—Hans I. Sun; Emil Moffa

[57] ABSTRACT

A method and apparatus for determining whether a slide is suitable for processing. A suite of suitability tests are performed by an automated microscope system. The tests include magnification error flags, staining flags, main optical density flags, including detected intermediate cell nuclei, rings around detected intermediate cell nuclei, average texture measure of detected intermediate cell nuclei, average contrast to detected intermediate cell nuclei to cytoplasm, standard deviation of detected intermediate cell nuclei optical densities, detected intermediate cell ratios, average stripe area, measure of a saturated magnification of the image, measure of a grossly saturated magnification, and the percentage of images focused properly on a first try, including images never focused properly. The automated microscope quantifies the measurements in a reliable and repeatable way.

22 Claims, 6 Drawing Sheets

OTHER PUBLICATIONS

Dytch, Harvey E. et al., "An Interactive Microcomputer-Based System for the Quantitative Analysis of Stratified Tissue Sections", *Analytical and Quantitative Cytology and Histology*, vol. 9, No. 1, pp. 69–78, Mar. 1987.

Enslein, Kurt and Peter W. Neurath, "Augmented Stepwise Discriminant Analysis Applied to Two Classification Problems in the Biomedical Field", *Computers and Biomedical Research*, 2, 568–581 (1969).

Kurman, Robert J. et al., "Part 1: Specimen Adequacy and Part 2: Descriptive Diagnoses", *The Bethesda System for Reporting Cervical/Vaginal Cytologic Diagnoses*, Springer-Verlag.

Weber, J.E. et al., "Fuzzy Reasoning, Possibility Theory and Probability Theory in Expert Systems for Histopathology", IEEE/Ninth Annual Conference of the Engineering in Medicine and Biology Society, pp. 1560–1562, ©1987.

Wied, G.L. et al., "Expert Systems as Classifiers in Diagnostic Cytopathology", IEEE/Ninth Annual Conference of the Engineering in Medicine and Biology Society, pp. 1915–1917, ©1987.

Wied, G.L. et al., "Expert System Design Under Uncertainty of Human Diagnosticians", IEEE/Eighth Annual Conference of the Engineering in Medicine and Biology Society, pp. 757–760, ©1986.

Wied, G.L. et al., "Ticas–Stratex, and Expert Diagnostic System For Stratified Cervical Epithelium", IEEE/Ninth Annual Conference of the Engineering in Medicine and Biology Society, pp. 1557–1559, ©1987.

Serra, J., *Image Analysis and Mathematical Morphology*, pp. 372–423, Academic Press, 1982.

Smith, Warren J., "Image Evaluation", *Modern Optical Engineering*, McGraw-Hill Book Company, 1966, pp. 308–325.

Patten, Jr., Stanley, "Diagnostic Cytopathology of the Uterine Cervix", Basel, Switzerland, Publisher: S. Karger, 1969, 2nd Edition 1978, Third volume in *Monographs in Clinical Cytology*, edited by G.L. Wied, pp. 10–15.

METHOD AND APPARATUS FOR DETECTION OF UNSUITABLE CONDITIONS FOR AUTOMATED CYTOLOGY SCORING

The invention relates to a slide suitability scoring apparatus and, more particularly, to a slide suitability scoring apparatus for an automated cytology system.

BACKGROUND OF THE INVENTION

A slide suitability score results from analyses applied to measurements of a slide's characteristics and an automated cytology system's effectiveness. Slide characteristics are properties of the biological sample on the slide and the slide itself such as bubble area, coverslip and mounting medium thickness, and staining properties. Automated cytology systems that score biological slides have an associated slide scoring effectiveness. Machine effectiveness measures, such as the percentage of requested fields of view that were focused adequately or the percentage of acquired images that had saturated pixels, are measures of how well the automated cytology system has begun to process a slide and how it proceeds to process a slide. For a particular slide, the slide suitability score determines the reliability of other types of slide scores, and thus, whether those scores should be reported. If a particular slide is anomalous, or if the automated cytology system did not operate effectively on the slide, it would be desirable to flag the unacceptable machine condition or slide characteristic so that potentially false results are not used.

SUMMARY OF THE INVENTION

The invention provides a method and apparatus for determining whether a slide is suitable for processing. The invention provides a suite of suitability tests that are performed by an automated microscope system. The tests include machine processing error flags, staining measures including mean detected intermediate cell nuclei stain, mean detected intermediate cell cytoplasm stain, mean texture of detected intermediate cell nuclei, mean contrast between detected intermediate cell nuclei and cytoplasm and standard deviation of detected intermediate cell nuclear stain, optical density, detected intermediate cell ratios, average stripe modulation patterns area, counts of saturated pixels within the images, the percentage of images focused properly on a first try, and the percentage of images never focused properly. The invention provides an apparatus to quantify these measurements in a reliable and repeatable way.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

DETAILED DESCRIPTION OF THE PREFERRED EMBODIMENT

Figure 1A:
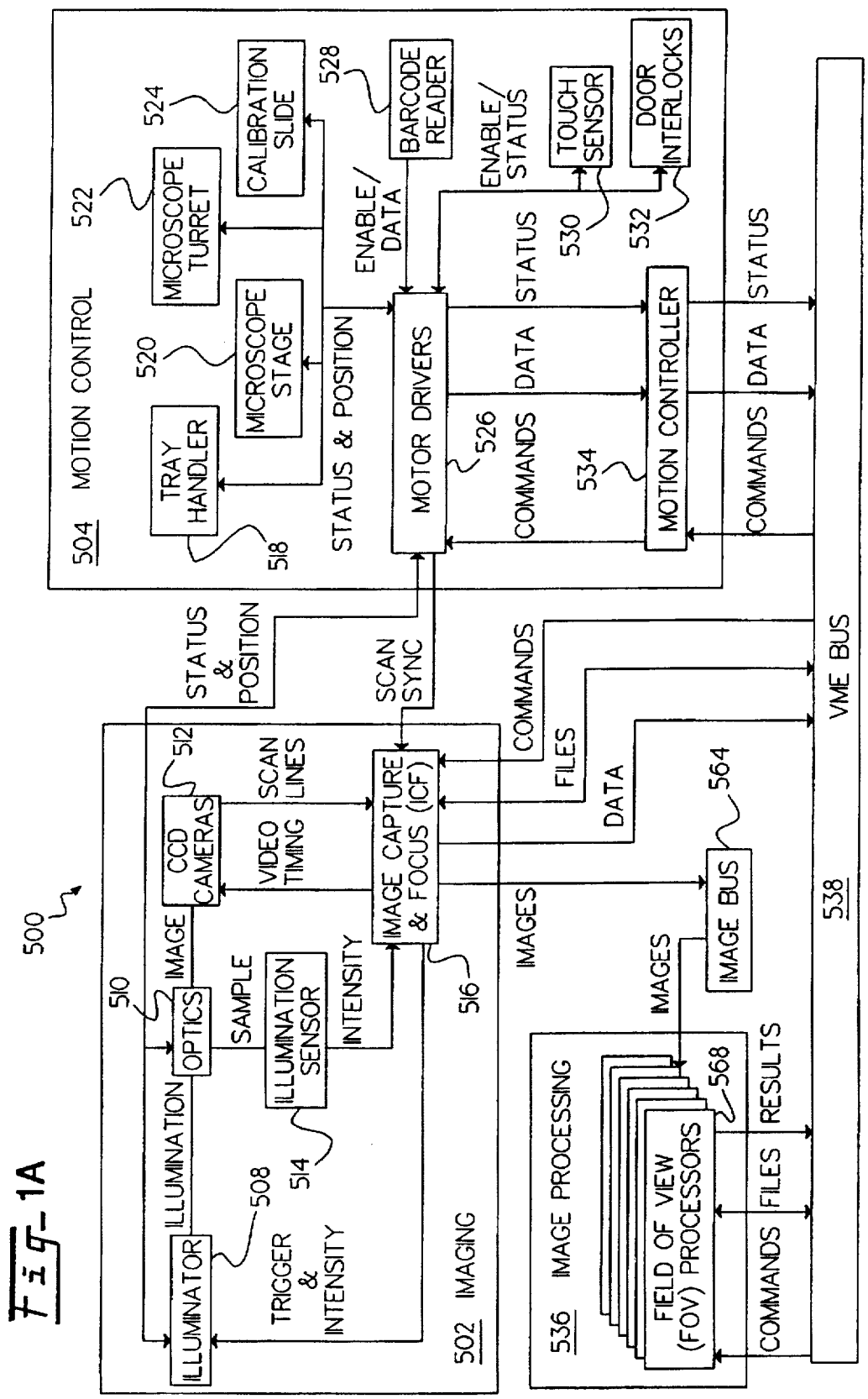
FIGS. 1A, 1B and 1C show the automated cytology screening apparatus of the invention.

The invention provides a method and apparatus for determining whether a slide is suitable for processing and has been processed properly. Unsuitability may stem from at least four different general sources:

1) specimen collection (physician related)

2) slide preparation (cell fixation by physician, staining at the lab, and slide materials used by the physician and laboratory), 3) slide handling (slide cleanliness and loading into automated microscope system), and 4) machine processing (failed or failing automated microscope system).

The invention provides a suite of suitability tests that are performed by an automated microscope system and which address each of the possible cause areas for unsuitability outlined above. The tests include:

1) specimen collection detected intermediate cell (reference cell) ratios percentage of images focused properly on a first try percentage of images never focused properly 2) slide preparation staining measures including:

mean detected intermediate cell nuclei, mean detected intermediate cell cytoplasm stain, mean texture of detected intermediate cell nuclei, mean contrast between detected intermediate cell nuclei and cytoplasm, and standard deviation of detected intermediate cell nuclear stain (optical density).

percentage of images focused properly on a first try percentage of images never focused properly 3) slide handling average stripe area counts of saturated image pixels 4) machine processing machine processing error flags (from automated feature range checking)

counts of saturated image pixels percentage of images focused properly on a first try percentage of images never focused properly Each test may apply to one or more of the unsuitability sources.

In a presently preferred embodiment of the invention, the system disclosed herein is used in a system for analyzing cervical pap smears, such as that shown and disclosed in U.S. patent application Ser. No. 08/571,686, filed Dec. 13, 1995, which is a file wrapper continuation of abandoned U.S. patent application Ser. No. 07/838,064, entitled "Method For Identifying Normal Biomedical Specimens", by Alan C. Nelson et al., filed Feb. 18, 1992; U.S. Pat. No. 5,528,703, which is a continuation in part of abandoned U.S. patent application Ser. No. 07/838,395, entitled "Method For Identifying Objects Using Data Processing Techniques", by S. James Lee, filed Feb. 18, 1992; U.S. patent application Ser. No. 07/838,070, now U.S. Pat. No. 5,315,700, entitled "Method And Apparatus For Rapidly Processing Data Sequences", by Richard S. Johnston et al., filed Feb. 18, 1992; U.S. patent application Ser. No. 07/838,065, now U.S. Pat. No. 5,361,140, entitled "Method and Apparatus for Dynamic Correction of Microscopic Image Signals" by Jon W. Hayenga et al.; and allowed U.S. patent application Ser.

No. 08/302,355, filed Sep. 7, 1994 entitled "Method and Apparatus for Rapid Capture of Focused Microscopic Images" to Hayenga et al., which is a continuation-in-part of application Ser. No. 07/838,063 filed on Feb. 18, 1992 the disclosures of which are incorporated herein, in their entirety, by the foregoing references thereto.

The present invention is also related to biological and cytological systems as described in the following patent applications which are assigned to the same assignee as the present invention, filed on Sep. 20, 1994 unless otherwise noted, and which are all hereby incorporated by reference including pending U.S. patent application Ser. No. 08/309,118, to Kuan et al. entitled, "Field Prioritization Apparatus and Method," pending U.S. patent application Ser. No. 08/309,061, to Wilhelm et al., entitled "Apparatus for Automated Identification of Cell Groupings on a Biological Specimen," pending U.S. patent application Ser. No. 08/309,116 to Meyer et al. entitled "Apparatus for Automated Identification of Thick Cell Groupings on a Biological Specimen," U.S. patent application Ser. No. 08/667,292, filed Jun. 20, 1996, which is a file wrapper continuation of abandoned U.S. patent application Ser. No. 08/309,115 to Lee et al. entitled "Biological Analysis System Self Calibration Apparatus," U.S. patent application Ser. No. 08/678,124, filed Jul. 11, 1996, which is a file wrapper continuation of abandoned U.S. patent application Ser. No. 08/308,992, to Lee et al. entitled "Apparatus for Identification and Integration of Multiple Cell Patterns," pending U.S. patent application Ser. No. 08/309,063, for which the issue fee has been paid, to Lee et al. entitled "Method for Cytological System Dynamic Normalization," pending U.S. patent application Ser. No. 08/309,248, for which the issue fee has been paid, to Rosenlof et al. entitled "Method and Apparatus for Detecting a Microscope Slide Coverslip," U.S. patent application Ser. No. 08/309,077 now U.S. Pat. No. 5,566,249 to Rosenlof et al. entitled "Apparatus for Detecting Bubbles in Coverslip Adhesive," pending U.S. patent application Ser. No. 08/309,931, to Lee et al. entitled "Cytological Slide Scoring Apparatus," pending U.S. patent application Ser. No. 08/309,148 to Lee et al., entitled "Method and Apparatus for Image Plane Modulation Pattern Recognition," pending U.S. patent application Ser. No. 08/309,250 to Lee et al. entitled "Apparatus for the Identification of Free-Lying Cells," and pending U.S. patent application Ser. No. 08/309,209 to Oh et al. entitled "A Method and Apparatus for Robust Biological Specimen Classification."

Figure 1B:
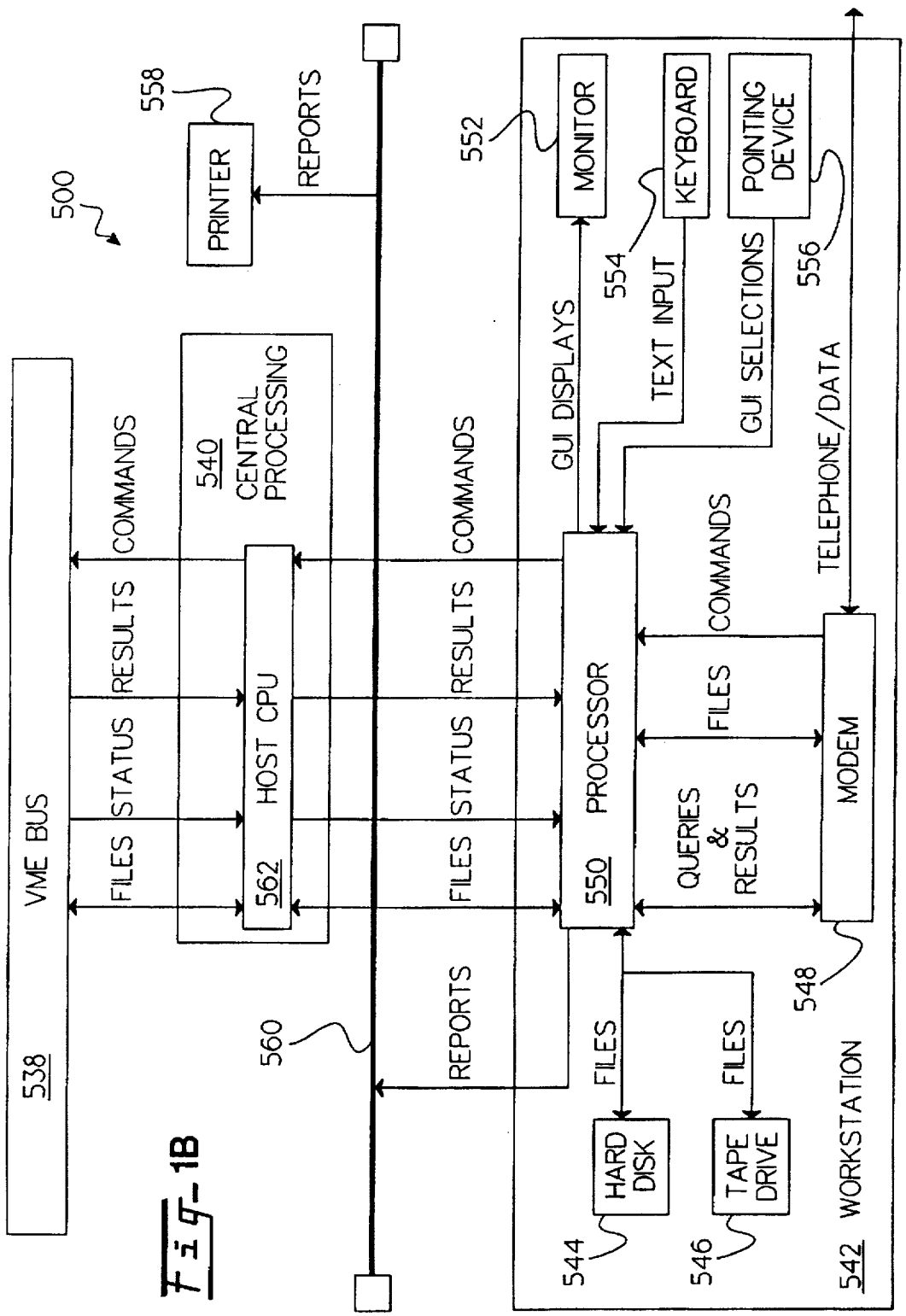
Figure 1C:
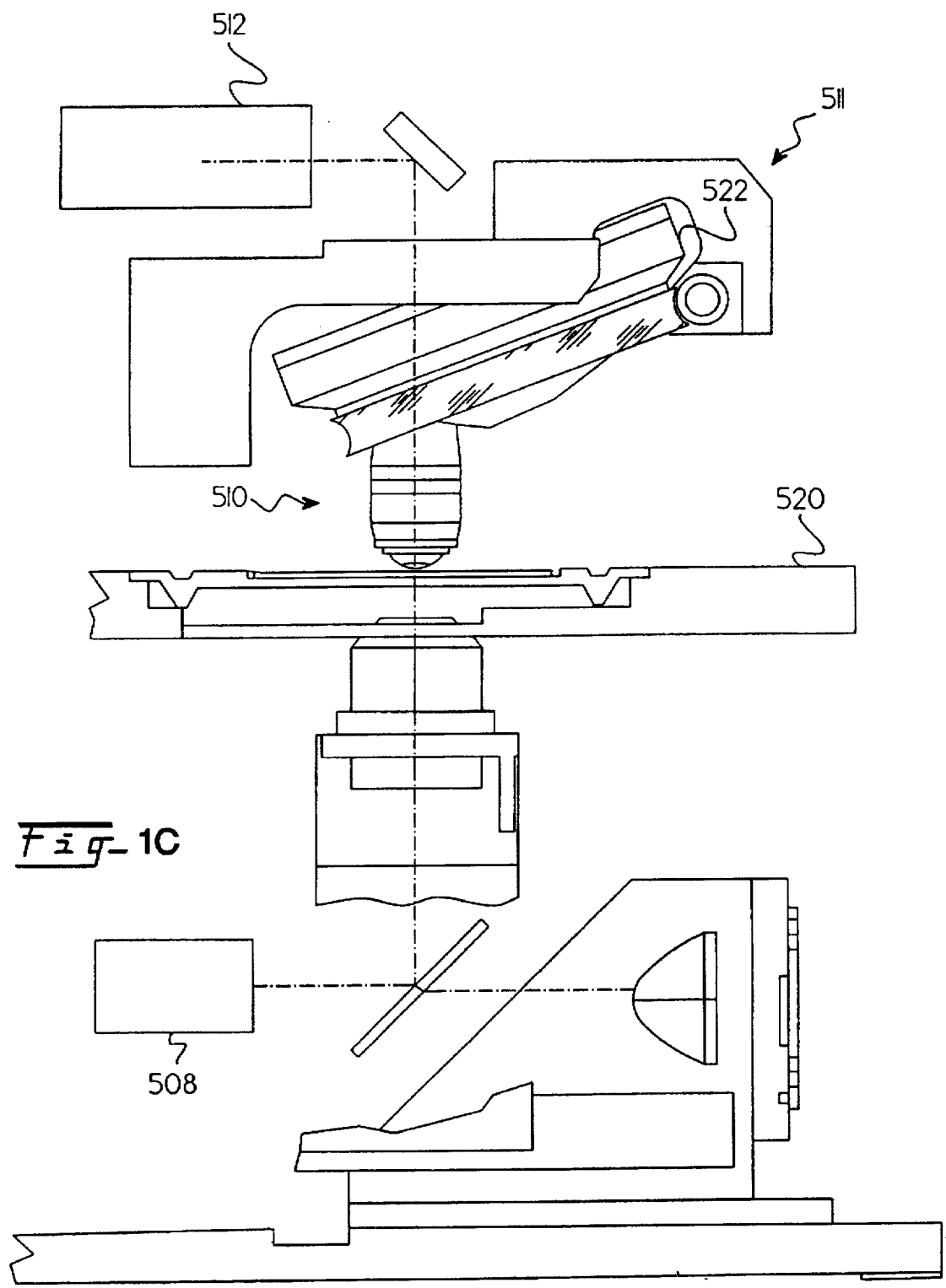

Now refer to FIGS. 1A, 1B and 1C which show a schematic diagram of one embodiment of the apparatus of the invention for field of view prioritization. The apparatus of the invention comprises an imaging system 502, a motion control system 504, an image processing system 536, a central processing system 540, and a workstation 542. The imaging system 502 is comprised of an illuminator 508, imaging optics 510, a CCD camera 512, an illumination sensor 514 and an image capture and focus system 516. The image capture and focus system 516 provides video timing data to the CCD cameras 512, the CCD cameras 512 provide images comprising scan lines to the image capture and focus system 516. An illumination sensor intensity is provided to the image capture and focus system 516 where an illumination sensor 514 receives the sample of the image from the optics 510. In one embodiment of the invention, the optics may further comprise an automated microscope 511. The illuminator 508 provides illumination of a slide. The image capture and focus system 516 provides data to a VME bus 538. The VME bus distributes the data to an image processing system 536. The image processing system 536 is comprised of field-of-view processors 568. The images are sent along the image bus 564 from the image capture and focus system 516. A central processor 540 controls the operation of the invention through the VME bus 538. In one embodiment the central processor 562 comprises a MOTOROLA 68030 (TM) CPU. The motion controller 504 is comprised of a tray handler 518, a microscope stage controller 520, a microscope tray controller 522, and a calibration slide 524. The motor drivers 526 position the slide under the optics. A bar code reader 528 reads a barcode located on the slide 524. A touch sensor 530 determines whether a slide is under the microscope objectives, and a door interlock 532 prevents operation in case the doors are open. Motion controller 534 controls the motor drivers 526 in response to the central processor 540. An Ethernet communication system 560 communicates to a workstation 542 to provide control of the system. A hard disk 544 is controlled by workstation 550. In one embodiment, workstation 550 may comprise a SUN SPARC CLASSIC (TM) workstation. A tape drive 546 is connected to the workstation 550 as well as a modem 548, a monitor 552, a keyboard 554, and a mouse pointing device 556. A printer 558 is connected to the ethernet 560.

During slide suitability testing, the central computer 540, running a real time operating system, controls the microscope 511 and the processor to acquire and digitize images from the microscope 511. The flatness of the slide may be checked, for example, by contacting the four corners of the slide using a computer controlled touch sensor. The computer 540 also controls the microscope 511 stage to position the specimen under the microscope objective, and from one to fifteen field of view (FOV) processors 568 which receive images under control of the computer 540.

It is to be understood that the various processes described herein may be implemented in software suitable for running on a digital processor. The software may be embedded, for example, in the central processor 540.

The processor 540 computes a suitability score that indicates whether a slide passed or failed any one of the following thirteen suitability tests. To pass and be suitable for reporting results, a slide must pass ALL of the tests. If a slide fails, the first test failed is identified. The thirteen tests are described as follows:

(1) if(twentyx_error_flag GE 0 AND fourx_error_count LE 0)

(2) if(stain GE 2.5 AND stain LE 8.0)

(3) if(st_mn_o GE 17.5 AND st_mn_o LE 45.0)

(4) if(st_nba GE 5.2 AND st_nba LE 7.6)

(5) if(st_ed_c GE −62.5 AND st_ed_c LE −32.0)

(6) if(sd_mn GE 7.0 AND sd_mn LE 30.0)

(7) if(int_rat GE 0.00017)

(8) if(aveStrAr LE 2800)

(9) if(sat_200 LE 0.07)

(10) if(st_5000 LE 0.02)

(11) if(s4×5000 LE 0.15)

(12) if(foc_1st GE 0.10)

(13) if(never LE 0.40)

TABLE 1

| Hazard ID | Description |
|---|---|
| Algorithms | Out of spec. staining |
| Algorithms | Density variations may cause misdiagnosis |

TABLE 1-continued

| Hazard ID | Description |
|---|---|
| Algorithms | Insufficient number of 20x images or excessive time to acquire |
| Electronic Chassis | Excess noise in images |
| Image Processing Computer | Intermittent failures due to external noise |
| Image Capture Processing | Degraded image quality (various) |
| Illumination | Degraded illumination (various) |
| Improper Optical Alignment | Excessive saturation due to misaligned camera |
| Laboratory Usage | Wrong slide type loaded into machine |
| System Focusing | False negative caused by poor focusing |

The suitability score detects conditions under which an automated screener will have performance limitations. These conditions were identified during suitability training and through system hazard analysis. Table 1 lists the system hazards that the slide suitability tests detect. In one embodiment the performance requirement of the suitability score is to score no more than 5% of the training slides as being unsuitable.

Figure 2:
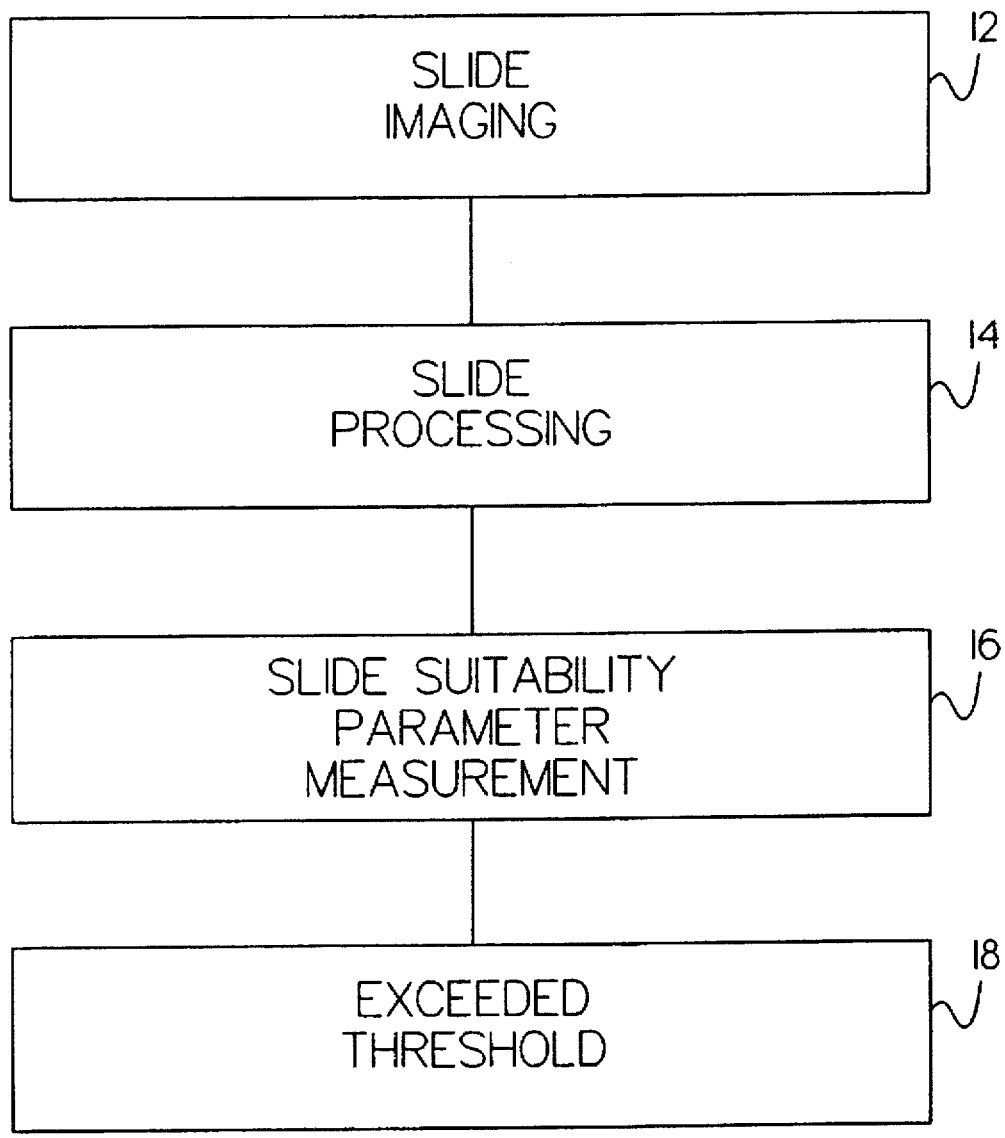
FIG. 2 shows the method of the invention to process a slide and determine if a suitability parameter has been exceeded.

Now refer to FIG. 2 which shows the method of the invention to process a slide. The invention images a slide in step 12. The slide is processed by the slide processing apparatus of the invention in step 14. In step 16 a slide suitability parameter is measured. In step 18 the process checks if the suitability parameter exceeds a predetermined threshold.

Additionally, the suitability score detects conditions that were not encountered during training. For example, if during training, stain measures for all slides ranged between 3 and 4, any slide that now measures 2 is outside that range, and as a result, unsuitable.

The suitability score also identifies slides on which algorithm processing errors were encountered; conditions where measures or processing parameters are unreasonable, or when processing parameters are unreasonable. As a result processing must cease. For example, if a function that contains objects returns a negative count, an algorithm processing error is flagged.

The first two features listed in table 2 are algorithm processing error flags. The next five features listed in table 2 are measures of the stain characteristics on the slide. All the stain features are calculated from objects that are identified by a detected intermediate cell classifier as detected intermediate cells. Clinicians use normal detected intermediate cells as reference cells against which all other cells on the slide can be compared. The eighth feature is a ratio of object counts. The ninth is output from the stripe detection algorithm. The last five measures relate to image acquisition performance.

Table 2 provides a short description of each measure used to test slide suitability. A detailed description of each features is also given later in this document.

TABLE 2

| Feature Name | Description |
|---|---|
| twentyx_error_flag | 20x processing flag |
| fourx_error_count | 4x processing flag |
| mean_stain_bin | Mean optical density of detected intermediate cell nuclei |
| st_outer_od | Mean optical density of a ring around the detected intermediate cell nuclei |
| st_nic_blur | Average texture measure of detected intermediate cell nuclei |
| st_edge_contrast | Average contrast of detected intermediate cell nuclei to cytoplasm |
| st_sd_mean_od | Standard deviation of detected intermediate cell nuclei optical densities |
| int_ratio | Detected intermediate cell ratio |
| ave_stripe_area | Average stripe area |
| sat_200 | Measure of saturated 20x images |
| sat_5000 | Measure of grossly saturated 20x |
| sat_4x_5000 | Measure of grossly saturated 4x |
| focus_first | Percent of 20x images focused properly on first try |
| never | Percent of 20x images never focused properly |

The computer processor 540 indicates whether a slide passed or failed the slide suitability tests, and in the case of failure, identifying which test failed.

Figure 3:
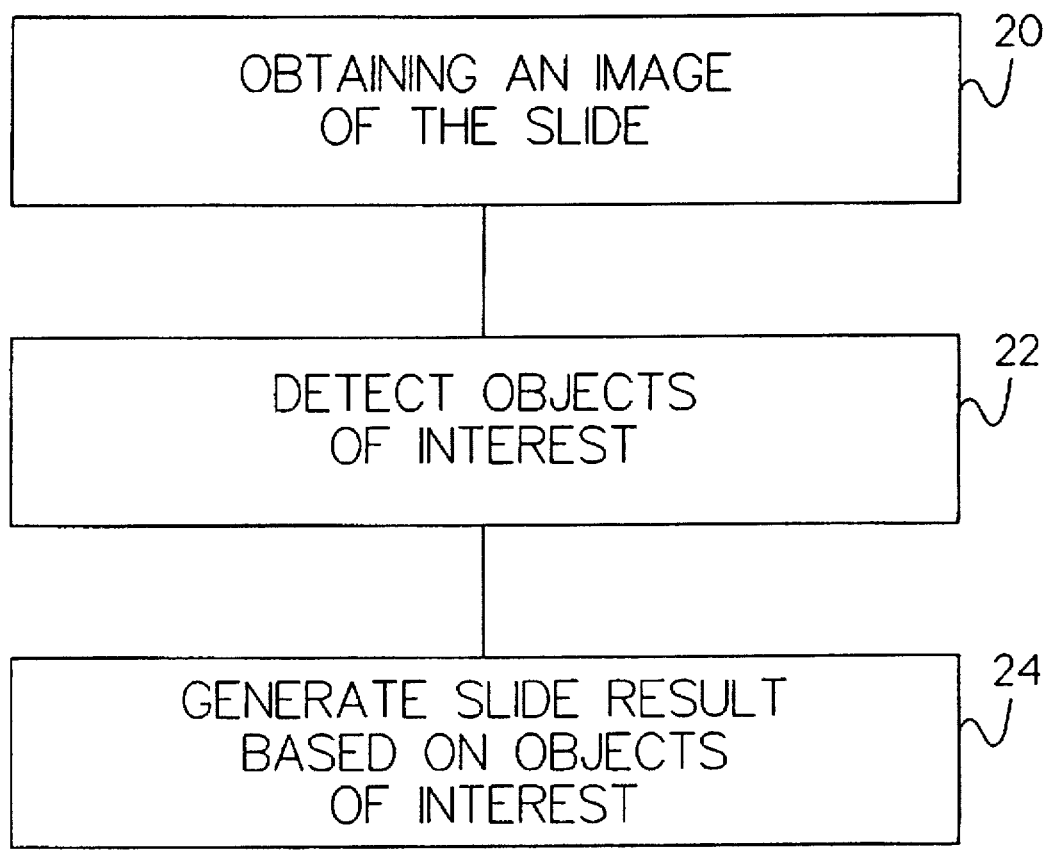
FIG. 3 shows the method of the invention to generate slide results.

Now refer to FIG. 3 which shows the method of the invention to process a slide. In step 20 the apparatus of the invention obtains an image of the slide. Objects of interest are detected from the image of the slide in step 22. The detected objects of interest are used to generate a slide result in step 24.

Feature Descriptions (1) twentyx_error_flag: A flag that is zero if no errors were encountered during 20× processing, less than zero if errors were encountered. This is implemented as the sum of all the values returned from slide processing at a 20× magnification.

(2) fourx_error_count: A flag that is zero if no errors were encountered during 4× processing, greater than zero if errors were encountered. This is implemented as the count of images for which a return value from 4× magnification processing was negative.

(3) stain: The mean bin value for detected intermediate cell nuclei on the slide that were detected by the first detected intermediate cell classifier. The mean optical density for each detected intermediate cell nucleus is calculated. Data for all the detected intermediate cell nuclei on the slide is accumulated in a 10-bin histogram.

(4) st__mn__o: The average of the following calculation for all detected intermediate cell nuclei on the slide. the mean of the optical density in an area produced by finding a 5×5 dilation residue minus a 5×5 closing of the nuclear mask, using a 2-pixel border, for each detected intermediate cell nucleus.

(5) st__nba: The nucleus of each detected intermediate cell is blurred using a 5×5 binomial filter. A residue is created as the absolute magnitude differences between the original and the blurred image. The average of the absolute magnitude differences is the nuclear blur average (nba). st__nba is the average nba for all detected intermediate cell nuclei on the slide.

(6) st__ed__c: First a dilation is calculated for each detected intermediate cell nucleus using a 5×5 structure element. The residue is then computed by subtracting the original image from the dilation. ed__c is the mean of the residue in a 2-pixel outer ring minus the mean of the residue in a 2-pixel inner ring. st__ed__c is the average ed__c for all detected intermediate cell nuclei on the slide.

(7) sd__mn: The standard deviation of the mean optical densities for all detected intermediate cell nuclei on the slide.

(8) int__rat: The number of objects identified as intermediate cells by the first intermediate cell classifier divided by the total number of objects detected by the single cell algorithm.

(9) aveStrAr: The average area segmented by the stripe modulation pattern algorithm. This is the total stripe area divided by the number of images in which stripes were segmented.

(10) sat__200: The percent of 20× images that have more than 200 pixels saturated. Each image that is acquired for processing is checked for saturation.

(11) st__5000: The percent of 20× images that have more than 5,000 pixels saturated.

(12) s4×5000: The percent of 4× images that have more than 5,000 pixels saturated.

(13) foc__1st: The percent of the first scan list of 20× images acquired in focus on the first try. During 20× image acquisition, system software acquires an image and then checks how well the image was focused. If the image was not focused well enough, another attempt at acquisition is made.

(14) never: The percent of the first scan list of 20× images that are never focused adequately.

Slide suitability performance is estimated from training data for tests 2–13 and is shown in Table 3. The numbers in the table represent the percentage and number, respectively, of slides rejected by the suitability classifier. Note that the Normal/Review and Abnormal/No Review columns should have high rejection numbers, while the Normal/No Review and Abnormal/Review columns should have low rejection numbers.

The invention has been constructed by NeoPath, Inc. of Bellevue, Wash. as the Autopap® 300 QC automated cytological slide classifier. Table 3 shows an example run on a set of test slides.

TABLE 3

Suitability Rejection of Slides by Type and Classification

| Normal slides QC | | Abnormal Slides QC | |
|---|---|---|---|
| No Review | Review | No Review | Review |
| 2.4% | 6.7% | 5.5% | 1.8% |
| 63/2576 | 41/613 | 46/843 | 48/2647 | n% = % of slides rejected
n/N = number of slides rejected/total number of training slides Overall, 3.0% of training slides are rejected; however, since most of the slides the AutoPap® 300 QC actually processes will be normal, the rejection figure is probably closer to 2.5%. This figure is well within the desired maximum of 5%.

Figure 4:
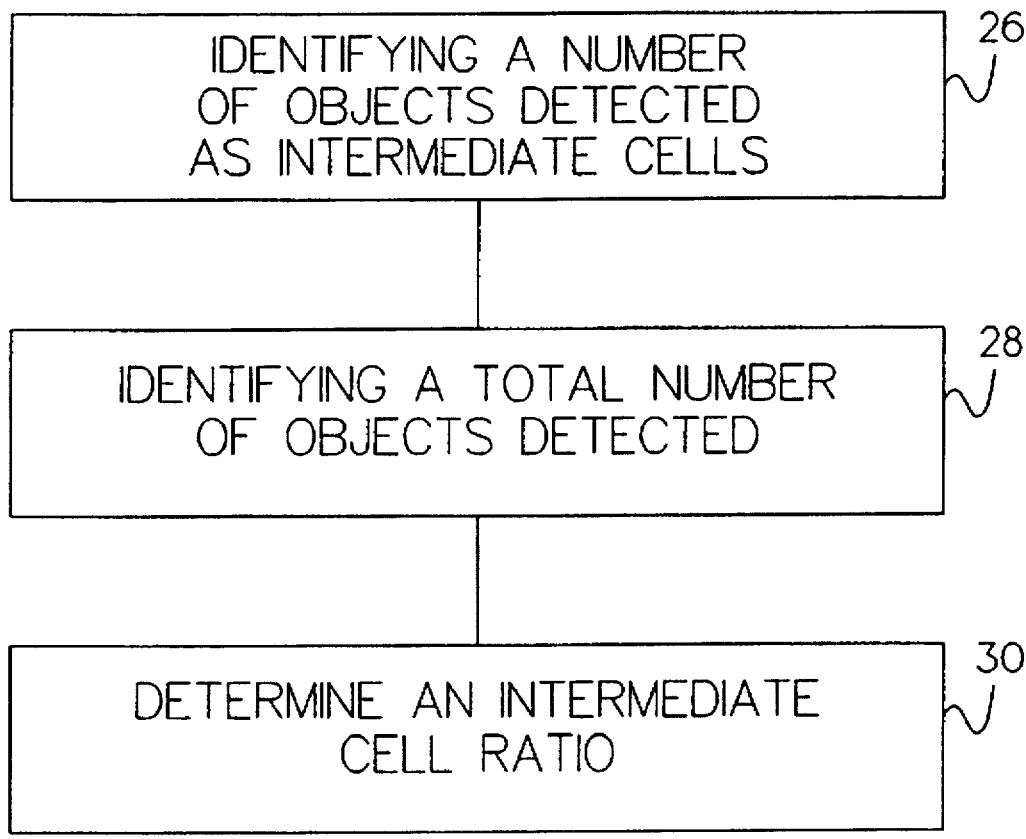
FIG. 4 shows the method of the invention to determine an intermediate cell ratio.

Refer now to FIG. 4 which shows the method of the invention to determine an intermediate cell ratio. First the slide is scanned to identify the number of objects that are detected as intermediate cells in step 26. The total number of objects that were detected is determined in step 28. In step 30 the intermediate cell ratio is computed by dividing the number of objects detected as intermediate cells by the total number of objects detected.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method of determining whether a slide processing system has suitably processed a biological specimen slide comprising the steps of:

(a) processing the biological specimen slide with the slide processing system;

(b) measuring at least one machine processing effectiveness parameter;

(c) checking if the at least one machine processing effectiveness parameter has exceeded a limit; and (d) accumulating scan processing error flags.

2. The method of claim 1 wherein the step of processing the biological specimen slide comprises:

(a) obtaining at least one image of the biological specimen slide;

(b) processing the at least one image of the biological specimen slide to detect at least one object of interest; and (c) scoring the slide as either normal or abnormal based on the at least one object of interest.

3. The method of claim 1 wherein the scan processing error flags are generated by checking if the at least one machine processing effectiveness parameter is within a range.

4. A method of determining whether a slide processing system has suitably processed a biological specimen slide comprising the steps of:

(a) processing the biological specimen slide with the slide processing system;

(b) measuring at least one machine processing effectiveness parameter;

(c) checking if the at least one machine processing effectiveness parameter has exceeded a limit; and (d) calculating at least one percentage of images that have more than at least one predetermined number of pixels saturated.

5. A method of determining whether a slide processing system has suitably processed a biological specimen slide comprising the steps of:

(a) processing the biological specimen slide with the slide processing system;

(b) measuring at least one machine processing effectiveness parameter;

(c) checking if the at least one machine processing effectiveness parameter has exceeded a limit; and (d) calculating at least one percentage of images acquired in focus on at least one predetermined number of tries.

6. A method of determining whether a slide processing system has suitably processed a biological specimen slide comprising the steps of:

(a) processing the biological specimen slide with the slide processing system;

(b) measuring at least one machine processing effectiveness parameter;

(c) checking if the at least one machine processing effectiveness parameter has exceeded a limit; and (d) calculating a percentage of images that were never adequately focused.

7. A method of determining whether a specimen collection result is suitable for automatic processing comprising the steps of:

(a) processing a slide to obtain at least one slide result;

(b) measuring at least one specimen collection result parameter;

(c) checking if at least one of the at least one specimen collection result parameters have exceeded a limit;

(d) identifying a number of objects detected as intermediate cells;

(e) identifying a total number of objects detected; and (f) dividing the number of objects detected as intermediate cells by the total number of objects detected to generate an intermediate cell ratio.

8. The method of claim 7 wherein intermediate cell nuclei are detected by an intermediate cell classifier, and wherein the intermediate cell nuclei has at least one feature value, further including the step of computing a mean of the at least one feature value over all detected intermediate cell nuclei.

9. The method of claim 8 wherein a mean optical density for each detected intermediate cell nucleus is calculated and a histogram of all intermediate cell optical densities is created.

10. The method of claim 9 further including the step of computing a standard deviation of mean optical densities for all detected intermediate cell nuclei on the slide.

11. The method of claim 8 further including the step of calculating an average feature value for all detected intermediate cell nuclei on the slide and calculating a mean of an optical density in an area produced by finding a dilation residue minus a closing of a nuclear mask for each detected intermediate cell nucleus.

12. The method of claim 8 further including the step of blurring a detected intermediate cell image using a binomial filter to create a blurred image.

13. The method of claim 12 further including the step of creating a residue image that is the magnitude of the difference between an original image and the blurred image.

14. The method of claim 13 wherein an average of the magnitude difference comprises a nuclear blur average.

15. The method of claim 8 further including the step of dilating the image of each detected intermediate cell to generate a dilated image.

16. The method of claim 15 further including the step of computing a residue image by subtracting the original image from the dilated image.

17. The method of claim 16 wherein an average of the residue image in a ring inside a nucleus is subtracted from a residue average in a ring outside the nucleus comprises an edge contrast value.

18. The method of claim 7 further including the step of calculating at least one percentage of images acquired in focus on at least one predetermined number of tries.

19. The method of claim 7 further including calculating a percentage of images that were never adequately focused.

20. A method of determining whether a slide handling result is suitable for automatic processing comprising the steps of:

(a) processing the slide;

(b) measuring at least one slide handling result parameter;

(c) checking if the at least one slide handling parameter has exceeded a limit; and (d) calculating at least one percentage of images that have more than at least one predetermined number of pixels saturated.

21. The method of claim 20 wherein the step of processing the slide comprises:

(a) obtaining at least one image of the slide;

(b) processing the at least one image of the slide to detect at least one object of interest; and (c) scoring the slide as either normal or abnormal based on the at least one object of interest.

22. The method of claim 20 further including the step of calculating an average area segmented by a modulation pattern detector as a total patterned area divided by a number of images in which modulation areas are detected.

\* \* \* \* \*